(12) United States Patent
Camerl

(10) Patent No.: US 11,980,567 B2
(45) Date of Patent: *May 14, 2024

(54) SURGICAL INFANT DIAPER

(71) Applicant: Timothy Camerl, Bristol, CT (US)

(72) Inventor: Timothy Camerl, Bristol, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,098

(22) Filed: Apr. 21, 2023

(65) Prior Publication Data

US 2023/0248565 A1 Aug. 10, 2023

Related U.S. Application Data

(63) Continuation of application No. 16/395,460, filed on Apr. 26, 2019, now Pat. No. 11,660,227.

(51) Int. Cl.
*A61F 5/453* (2006.01)
*A61F 5/44* (2006.01)
*A61F 13/471* (2006.01)
*A61F 13/84* (2006.01)

(52) U.S. Cl.
CPC ............ *A61F 5/453* (2013.01); *A61F 5/4401* (2013.01); *A61F 13/471* (2013.01); *A61F 13/84* (2013.01)

(58) Field of Classification Search
CPC ...... A61F 5/453; A61F 13/471; A61F 5/4401; A61F 13/84; A61F 2005/4402; A61F 13/4915
See application file for complete search history.

(56) References Cited

U.S. PATENT DOCUMENTS

| | | | | |
|---|---|---|---|---|
| 1,895,343 A | * | 1/1933 | Pickett | A61B 46/30 2/408 |
| 4,019,517 A | * | 4/1977 | Glassman | A61F 13/493 604/397 |
| 5,074,853 A | * | 12/1991 | Bryant | A61F 5/4401 604/385.19 |
| 6,979,325 B2 | | 12/2005 | Reddy | |
| 2004/0143232 A1 | * | 7/2004 | Perez | A61F 13/4915 604/385.09 |
| 2007/0197983 A1 | | 8/2007 | Finn | |
| 2013/0006208 A1 | * | 1/2013 | Close | A61F 13/471 604/385.09 |
| 2016/0022509 A1 | | 1/2016 | Reddy | |
| 2016/0346137 A1 | * | 12/2016 | Villarreal | A61F 5/4401 |

* cited by examiner

*Primary Examiner* — Benjamin J Klein
*Assistant Examiner* — Gabriella E Burnette
(74) *Attorney, Agent, or Firm* — Boudwin Intellectual Property Law, LLC; Daniel Boudwin

(57) ABSTRACT

A surgical infant diaper. The surgical infant diaper includes a flexible body having an interior layer and an exterior layer, wherein the flexible body further includes a front portion, a rear portion, and a central portion therebetween. The flexible body is movable between an open position and a closed position, wherein the closed position an upper opening and a pair of leg openings are defined. A central aperture extends through the front portion, wherein the central aperture is positioned to receive a penis of the wearer therethrough.

9 Claims, 3 Drawing Sheets

SURGICAL INFANT DIAPER

CROSS REFERENCE TO RELATED APPLICATIONS

This application claims the benefit of U.S. Provisional Application No. 62/663,425 filed on Apr. 27, 2018 and is a continuation of U.S. Non-Provisional application Ser. No. 16/395,460 filed on Apr. 26, 2019. The above identified patent applications are herein incorporated by reference in its entirety to provide continuity of disclosure.

BACKGROUND OF THE INVENTION

The present invention relates to surgical infant diapers. More particularly, the present invention pertains to surgical infant diapers having a central aperture configured to receive a penis of the user therethrough, such that waste, blood, and urine are contained away from a surgical site.

Surgical intervention is often required in infants to correct birth defects or other malformations of body parts. Specifically, areas around the genitals may need to be corrected for various reasons, including, but not limited to, hypospadias, in which the urinary opening is not located in the usual place. These operations often lead to extended healing periods, while the surgical site recovers. Traditionally, diapers are worn during this period, in addition to bandages, however traditional diapers fail to separate fecal matter from the surgical site, potentially leading to infection. Additionally, drains or catheters may be required during the healing process, which a traditional diaper would prevent. Therefore, a diaper that separates the surgical site from waste from the infant, while also providing access for drains and catheters is desired.

In light of the devices disclosed in the known art, it is submitted that the present invention substantially diverges in design elements from the known art and consequently it is clear that there is a need in the art for an improvement to existing surgical infant diapers. In this regard, the instant invention substantially fulfills these needs.

SUMMARY OF THE INVENTION

In view of the foregoing disadvantages inherent in the known types of surgical infant diapers now present in the known art, the present invention provides a surgical infant diaper wherein the same can be utilized for providing convenience for the user when maintaining hygiene around a surgical site located around an infant's penis.

The present system comprises a flexible body comprising an interior layer and an exterior layer. The flexible body further comprises a front portion, a rear portion, and a central portion extending therebetween, such that the flexible body is selectively movable between an open position and a closed position, thereby defining an upper opening and a pair of leg openings. A central aperture is disposed through the front portion, the central aperture positioned to receive a penis of the wearer therethrough. In some embodiments, the central portion comprises a width less than that of each of the front portion and the rear portion. In another embodiment, the front portion and the rear portion gradually taper towards the central portion. In other embodiments, a pair of tabs are affixed to opposing sides of a distal end of the rear portion, wherein the pair of tabs are configured to removably secure to fasteners disposed on an exterior surface of the front portion, such that the flexible body is retained in the closed position.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
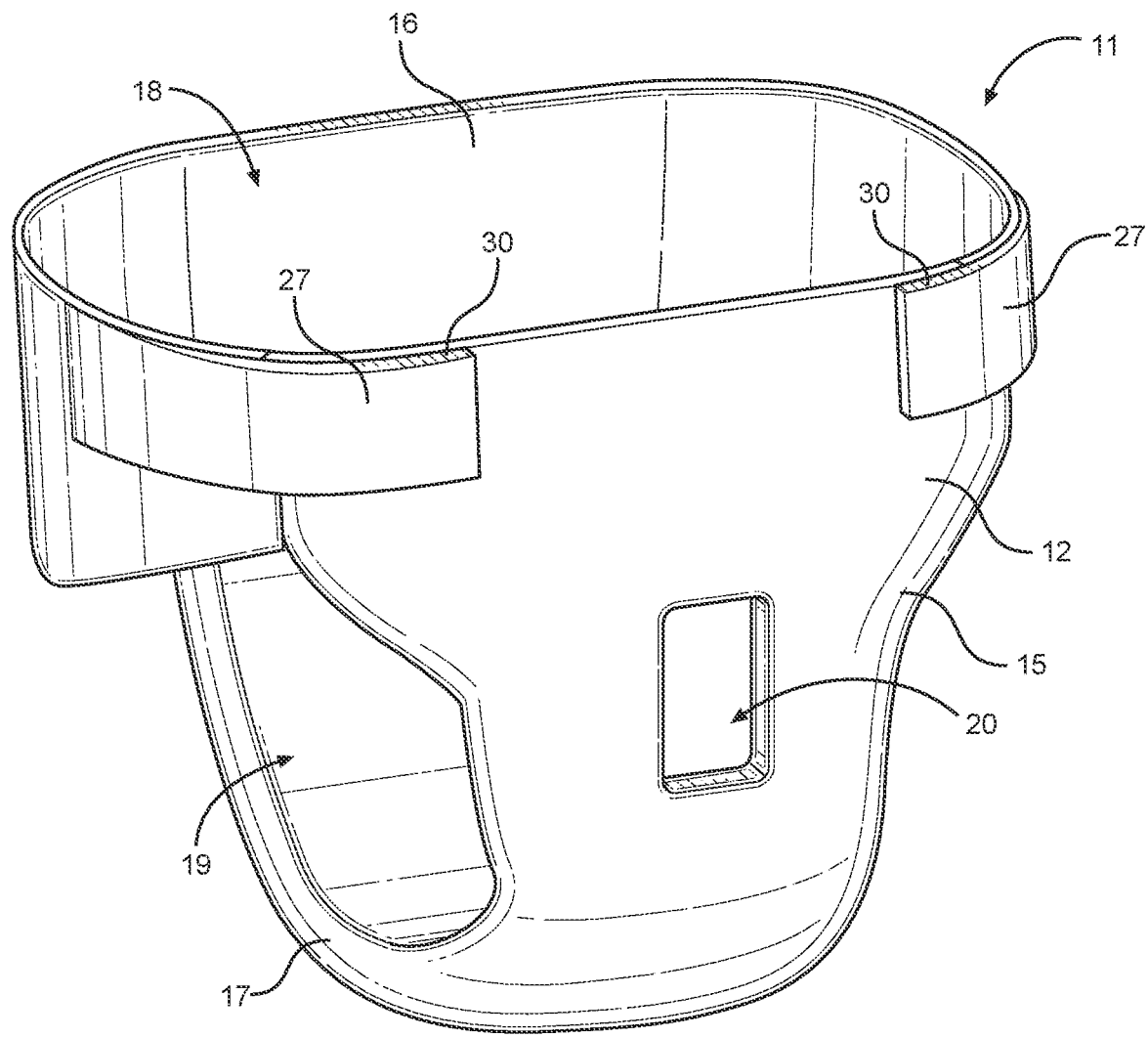
FIG. 1 shows a perspective view of an embodiment of the surgical infant diaper.

Reference is made herein to the attached drawings. Like reference numerals are used throughout the drawings to depict like or similar elements of the surgical infant diaper. The figures are intended for representative purposes only and should not be considered to be limiting in any respect.

Referring now to FIG. 1, there is shown a perspective view of an embodiment of the surgical infant diaper in the closed position. The surgical infant diaper 11 comprises a flexible body 12 having a front portion 15, a rear portion 16, and a central portion 17 extending therebetween, thereby connecting the front portion 15 to the rear portion 16. A central aperture 20 is disposed through the front portion 15, wherein the central aperture 20 is positioned along the front portion 15 to receive a penis of a wearer of the surgical infant diaper 11 therethrough. In this way, the wearer's penis, and any related surgical sites therearound, are exposed and separated from the interior of the surgical infant diaper 11, thereby minimizing infection risk of the surgical site by waste collected within the surgical infant diaper 11.

Figure 3:
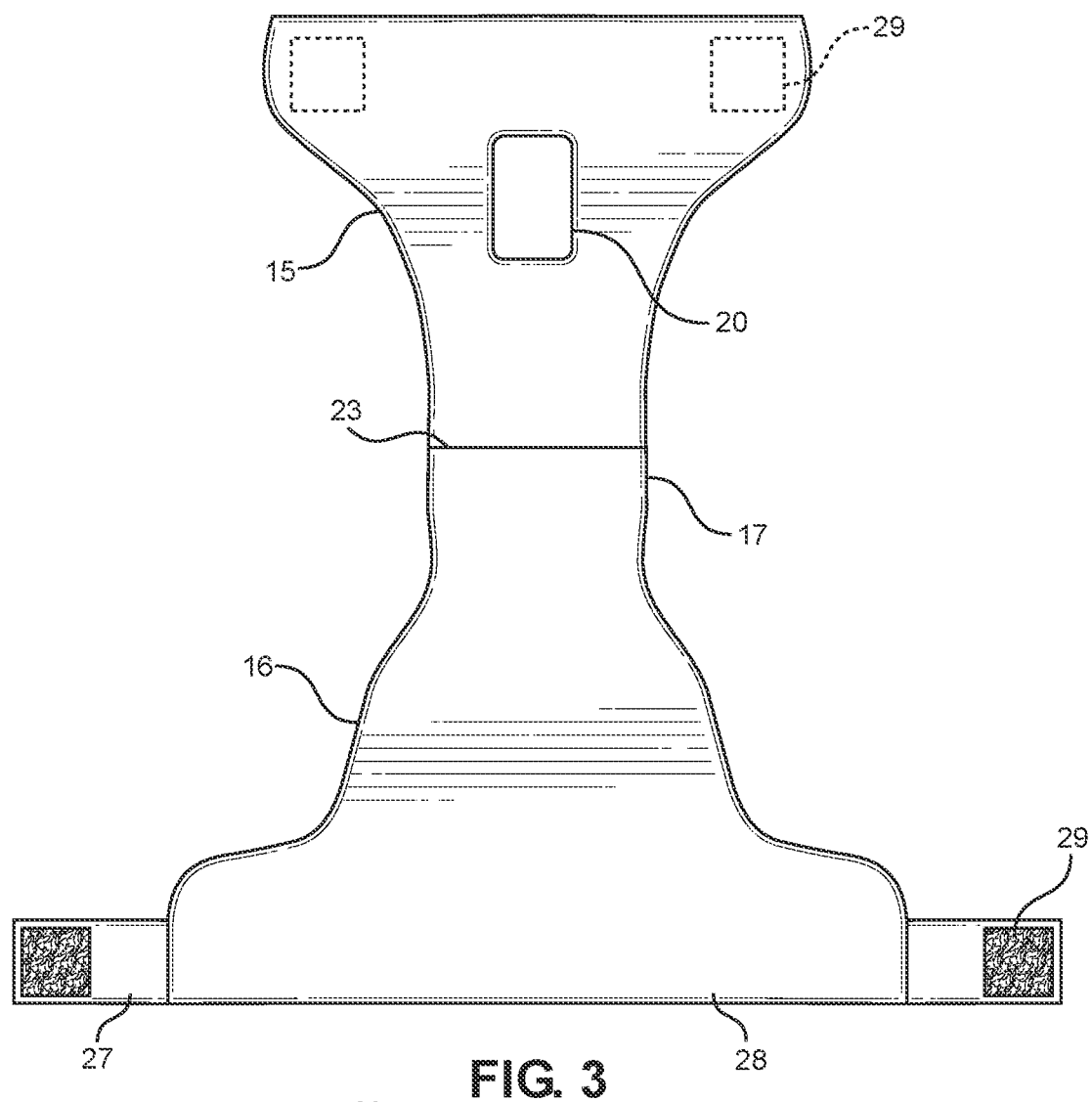
FIG. 3 shows a top plan view of an embodiment of the surgical infant diaper.

The flexible body 12 is selectively movable between an open position (as shown in FIG. 3), and a closed position (as shown in FIG. 1), wherein the closed position the surgical infant diaper 11 is configured to conform to a wearer's lower body. Further, when in the closed position, the shape of the front portion 15 relative to each of the central portion 17 and the rear portion 16 defines an upper opening 18 and a pair of leg openings 19. The upper opening 18 is configured to receive a torso of the wearer therethrough, while the pair of leg openings 19 are each configured to receive a leg of the wearer therethrough. In some embodiments, a perimeter of each of the pair of leg openings 19 comprise an elastic material therein, such that the pair of leg openings 19 are biased radially inwardly thereby forming a seal between the pair of leg openings 19 and the leg of the wearer to minimize any risk of waste leakage therethrough. Similarly, in another embodiment, the upper opening 18 further comprises an elastic material therein, such that the upper opening is biased radially inwardly, thereby forming a seal about the torso of the user to minimize the risk of waste leakage therethrough. In the illustrated embodiment, a pair of tabs 27 are affixed to the rear portion 16 along a distal end (as shown in FIG. 3, 28) thereof. The pair of tabs 27 are configured to removably secure to the front portion 15, such that the flexible body 12 is retained in the closed position. In the illustrated embodiment, an upper edge 30 of the pair of tabs 27 rests flush with the upper opening 18. In this way, the upper opening 18 a seal is formed between the wearer and the upper opening 18, thereby minimizing the risk of any waste leakage therethrough.

Figure 2:
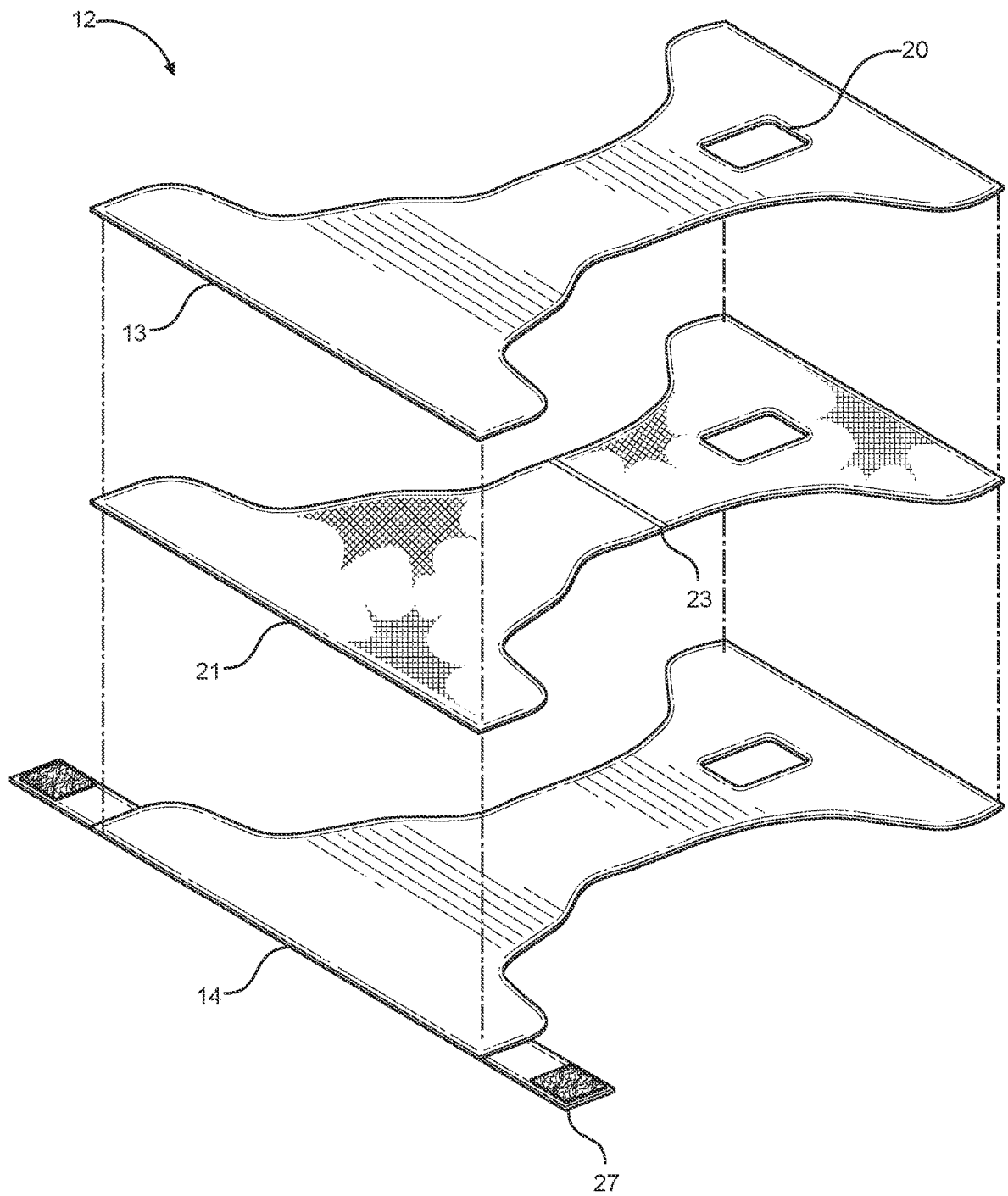
FIG. 2 shows an exploded view of an embodiment of the surgical infant diaper.

Referring now to FIG. 2, there is shown an exploded view of an embodiment of the surgical infant diaper. In the illustrated embodiment, the flexible body 12 comprises an interior layer 13, and exterior layer 14, and an absorbent layer 21 therebetween. The interior layer 13 is configured to wick fluid from an interior of the flexible body 12, thereby minimizing fluid contact with the wearer. In embodiments having the absorbent layer 21, the absorbent layer 21 serves to collect greater quantities of fluid therein, further separating fluid from the wearer, while also allowing increased storage capacity. In this way, in situations where the surgical infant diaper cannot be readily changed for a clean diaper, the surgical infant diaper can be used for longer periods of time before changing is required. In some embodiments, the exterior layer 14 comprises a fluid impermeable material, such that fluid stored within the interior layer 13 or the absorbent layer 21 does not seep therethrough, thereby preventing soiling of the surrounding area during use.

In the illustrated embodiment, the absorbent layer 21 further comprises a fluid impermeable barrier 23 extending thereacross between the front portion and the rear portion. In this way, fecal matter and other fluid waste collected in the rear portion of the surgical infant diaper does not travel from the rear portion towards the front portion, thereby isolating the surgical site further. This further decreases the risk of infection from contact with waste fluids. Furthermore, in the illustrated embodiment, the pair of tabs 27 are disposed on the exterior layer 14, such that the pair of tabs 27 are separated from any waste collected within the interior layer 13 or the absorbent layer 21. In this way, the pair of tabs 27 are maintained in a clean state during use, such that a user can easily remove the surgical infant diaper without directly contacting waste therein.

Referring now to FIG. 3, there is shown a top plan view of an embodiment of the surgical infant diaper in an open position. In the illustrated embodiment, the flexible body comprises a front portion 15 connected to a rear portion 16 via a central portion 17 extending therebetween. In the illustrated embodiment, the front portion 15 and the rear portion 16 taper inwardly towards the central portion 17, such that the central portion 17 comprises a width less than that of each of the front portion 15 and the rear portion 16. In this way, the flexible body is configured to conform to the lower torso of the user, such that the central portion 17 extends between a wearer's legs. In the illustrated embodiment, the rear portion 16 comprises a width greater than that of the front portion 15, such that the rear portion 16 can wrap about the torso of the wearer and removably secure to the front portion 15. Furthermore, in the shown embodiment, the rear portion 16 tapers at varying rates such that a rear of the wearer is fully covered thereby, while simultaneously providing additional width for encircling the wearer.

In the illustrated embodiment, the rear portion 16 further comprises the pair of tabs 27 extending from opposing ends thereof at a distal end 28 of the rear portion 16. Further, in the shown embodiment, the pair of tabs 27 further comprise fasteners 29 thereon, wherein the fasteners 29 are configured to removably secure to complementary fasteners 29 disposed on an exterior of the front portion 15. In some embodiments, the fasteners 29 comprise hook and loop fasteners, however, alternate fastening methods are contemplated. In the illustrated embodiment, the pair of tabs 27 extend from the distal end 28, such that the upper edge of each of the pair of tabs 27 is flush with the distal end 28. In this way, the distal end 28 forms a seal about the torso of the wearer when the surgical infant diaper is in the closed position.

In the illustrated embodiment, the central portion 17 further comprises a fluid impermeable barrier 23 thereacross, such that the barrier 23 separates the front portion 15 from the rear portion 16. In this way, fluid is prevented from traveling between the front portion 15 and the rear portion 16, thereby minimizing infection risk for the surgical site disposed about the central aperture 20. In some embodiments, the barrier 23 comprises a fluid impermeable material extending across a width of the central portion 17. In other embodiments, the rear portion 16 is separate from the front portion 15, such that waste material cannot pass therebetween.

Figure 4:
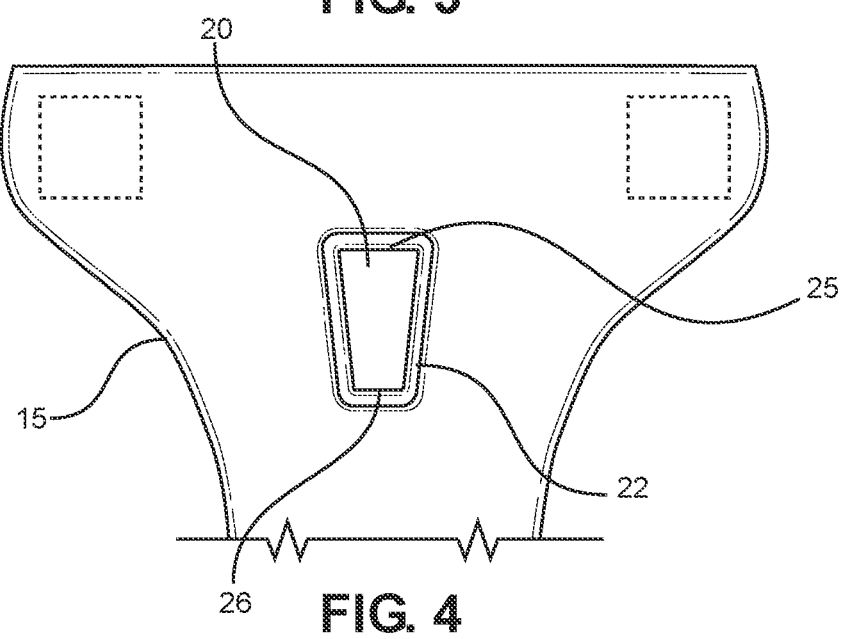
FIG. 4 shows a close-up view of the central aperture of an embodiment of the surgical infant diaper.

Referring now to FIG. 4, there is shown a close-up view of the central aperture of an embodiment of the surgical infant diaper. In the illustrated embodiment, the central aperture 20 tapers from an upper end 25 thereof towards a lower end 26 thereof, such that the upper end 25 comprises a greater width than the lower end 26. In this way, the area immediately surrounding the surgical site is kept at a greater distance from a perimeter 22 of the central aperture 20, thereby ensuring maximal comfort, while also minimizing the risk of waste material disposed in the front portion 15 contacting the surgical site. Additionally, in the shown embodiment, the perimeter 22 of the central aperture 20 comprises an absorbent material, such that any seepage from the surgical site is captured thereby and is thus wicked away from the surgical site. In the illustrated embodiment, a diameter of the central aperture through the absorbent layer is less than a diameter of the central aperture through the interior layer and the exterior layer, such that the perimeter 22 comprises a portion of the absorbent layer extending beyond a border of the central aperture disposed through each of the interior and exterior layers. In some embodiments, the perimeter 22 comprises a lip extending from the absorbent layer, such that the perimeter 22 comprises a portion of the absorbent layer resting flush with the interior and exterior layers through the central aperture 20. In this way, the perimeter 22 efficiently wicks fluid away from the surgical site, as no fluid transfer between differing materials, having different absorption rates, is required.

In one exemplary use, the user would secure the surgical infant diaper about the lower torso of the wearer, such that the penis of the user extends through the central aperture 20. In this way, the surgical site is exposed for more efficient bandage changing, while also keeping the surgical site sterile in light of waste fluids collecting within the diaper. The surgical infant diaper is secured about the wearer by securing the pair of tabs to the front portion 15, such that the fasteners thereon removably secure to complementary fasteners on the front portion 15. Should waste accumulate within the surgical infant diaper, the user can replace the soiled diaper with a new clean diaper in a similar manner. In this way, the user can keep waste away from the surgical site, thereby minimizing infection risk, while simultaneously providing easy access to the surgical site for bandage changing purposes, as well as drainage or catheter needs.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A surgical infant diaper, comprising:
    a flexible body comprising an interior layer and an exterior layer;
    wherein the flexible body further comprises a front portion;
    wherein the flexible body is selectively movable between an open position and a closed position, wherein the closed position, an upper opening and a pair of leg openings are defined thereby;
    a central aperture disposed through the interior layer and the exterior layer of the front portion, the central aperture positioned to receive a penis of a wearer therethrough;
    an absorbent layer disposed between the interior layer and the exterior layer, wherein the central aperture extends through the absorbent layer;
    wherein a diameter of the central aperture through the absorbent layer is less than a diameter of the central aperture through the interior layer and the exterior layer.

2. The surgical infant diaper of claim 1, wherein a perimeter of the central aperture comprises a lip extending from the absorbent layer, such that the perimeter comprises a portion of the absorbent layer resting flush with the interior layer and the exterior layer.

3. The surgical infant diaper of claim 1, wherein the absorbent layer further comprises a barrier configured to prevent fluid absorbed into the absorbent layer from transferring from the front portion.

4. The surgical infant diaper of claim 1, wherein a perimeter of the pair of leg openings comprises an elastic material therein, such that the pair of leg openings are biased radially inwardly.

5. The surgical infant diaper of claim 1, wherein the central aperture tapers inwardly from an upper side thereof towards a lower side thereof.

6. The surgical infant diaper of claim 1, wherein the upper opening further comprises an elastic material therein, such that the upper opening is biased radially inwardly.

7. The surgical infant diaper of claim 1, wherein a pair of tabs extend from opposing ends, wherein the pair of tabs comprise fasteners thereon, the fasteners configured to removably secure to complementary fasteners disposed on an exterior surface of the front portion.

8. The surgical infant diaper of claim 1, wherein the exterior layer comprises a fluid impermeable material.

9. A surgical infant diaper, comprising:
    a flexible body comprising an interior layer and an exterior layer;
    wherein the flexible body further comprises a front portion;
    a pair of tabs affixed to opposing sides;
    wherein the flexible body is selectively movable between an open position and a closed position, wherein the closed position, an upper opening and a pair of leg openings are defined thereby;
    wherein the pair of tabs are configured to removably secure to fasteners disposed on an exterior surface of the front portion, such that the flexible body is retained in the closed position;
    wherein an upper edge of each of the pair of tabs is flush with the upper opening;
    a central aperture disposed through the interior layer and the exterior layer of the front portion, the central aperture positioned to receive a penis of a wearer therethrough;
    an absorbent layer disposed between the interior layer and the exterior layer, wherein the central aperture extends through the absorbent layer;
    wherein a diameter of the central aperture through the absorbent layer is less than a diameter of the central aperture through the interior layer and the exterior layer.

* * * * *